(12) United States Patent
Lin et al.

(10) Patent No.: US 11,815,484 B2
(45) Date of Patent: Nov. 14, 2023

(54) DEVICE FOR MEASURING COMPLEX DIELECTRIC PERMITTIVITY OF A MATERIAL-UNDER-TEST, MEASURING DEVICE FOR MULTIPLE REFLECTIONS OF TIME-DOMAIN SIGNALS OF A COMPLEX DIELECTRIC AND MEASURING METHOD THEREOF

(71) Applicant: National YANG MING Chiao Tung University, Hsinchu (TW)

(72) Inventors: Chih-Ping Lin, Hsinchu (TW); Yin Jeh Ngui, Hsinchu (TW)

(73) Assignee: NATIONAL YANG MING CHIAO TUNG UNIVERSITY, Hsinchu (TW)

(*) Notice: Subject to any disclaimer, the term of this patent is extended or adjusted under 35 U.S.C. 154(b) by 0 days.

(21) Appl. No.: 17/748,314

(22) Filed: May 19, 2022

(65) Prior Publication Data
US 2023/0194455 A1    Jun. 22, 2023

(30) Foreign Application Priority Data

Dec. 16, 2021    (TW) .................................. 110147291

(51) Int. Cl.
*G01N 27/22* (2006.01)
(52) U.S. Cl.
CPC .................. *G01N 27/221* (2013.01)
(58) Field of Classification Search
CPC .................................................. G01N 27/221
See application file for complete search history.

(56) References Cited

U.S. PATENT DOCUMENTS

2019/0196047 A1\* 6/2019 Chaney .................... G01V 3/30

OTHER PUBLICATIONS

Lin et al., "Multiple Reflection Analysis of TDR signal for Complex Dielectric Spectroscopy" (Year: 2018).\*

\* cited by examiner

*Primary Examiner* — Feba Pothen
(74) *Attorney, Agent, or Firm* — Volpe Koenig (57) ABSTRACT

A device for measuring the complex dielectric permittivity of a material under test (MUT) includes an electromagnetic wave generating/receiving unit, a transmission line, a self-referencing waveguide section and a sensing waveguide section. The electromagnetic wave generating/receiving unit is configured to generate an electromagnetic wave signal. The transmission line has a first characteristic impedance and transmits the electromagnetic wave signal. The self-referencing waveguide section has a second characteristic impedance, and includes a front end and a back end, wherein a first reflection signal is sent from the front end. The sensing waveguide section is connected to the back end, and configured to cooperate with the back end to send out remaining subsequent reflection signals, wherein the electromagnetic wave generating/receiving unit receives the first reflection signal and the remaining subsequent reflection signals to measure the complex dielectric permittivity of the MUT.

19 Claims, 6 Drawing Sheets

DEVICE FOR MEASURING COMPLEX DIELECTRIC PERMITTIVITY OF A MATERIAL-UNDER-TEST, MEASURING DEVICE FOR MULTIPLE REFLECTIONS OF TIME-DOMAIN SIGNALS OF A COMPLEX DIELECTRIC AND MEASURING METHOD THEREOF

CROSS-REFERENCE TO RELATED APPLICATION AND CLAIM OF PRIORITY

The application claims the benefit of Taiwan Application No. 110147291, filed on Dec. 16, 2021, at the TIPO, the disclosures of which are incorporated herein in their entirety by reference.

FIELD OF THE INVENTION

The present invention is related to a device for measuring the broadband complex dielectric permittivity (CDP) of a material under test and its measurement method, and particularly is related to a waveguide device for measuring the broadband CDP of the material under test, and its measurement method.

BACKGROUND OF THE INVENTION

The method of measuring the dielectric spectrum of a material under test (MUT) based on a vector network analyzer (VNA) is time-consuming, tedious, expensive, and requires complex system calibrations. Fast and simple measurement techniques (e.g., capacitance probes and travel-time-based time-domain reflectometry (TDR) measurements) can only measure single-valued equivalent permittivity without information on the frequency and real and imaginary parts of the dielectric permittivity. Traditional TDR dielectric spectroscopy (Time Domain Spectroscopy, TDS) offers a more economical alternative compared to VNAs, but it is less accurate due to uncertainty in the characterization of the input function, and its probe design is inconvenient. The emerging TDR dielectric spectroscopy technique does not require a known input function, but is less accurate in the measurement of dispersive substances, and the measurable frequency bandwidth is limited.

In the essay of Brunfeldt & Mukherjee, 1995 (Brunfeldt, D R, & Mukherjee, S. (1995). Vector network analyzer (Canada Patent No. CA2030272C)), the vector network analyzer uses existing broadband dielectric spectrum analyzers (e.g., vector network analyzers) to detect the dielectric properties of the material under test, which is time-consuming, tedious, expensive, and require complex system calibration. The VNA uses a multi-frequency sweep procedure to measure a wide-band dielectric spectrum. As the target bandwidth and frequency resolution increase, the time to acquire the dielectric spectrum of the material under test will increase. Furthermore, the preparation and volume of the sample to be tested using VNA is not easy for measurements in certain medium such as soil. Due to the sophistication of the instrument and the complexity of calibration, VNA technique does not allow the flexibility and convenience of dielectric spectrum analysis. This is especially true when it comes to measurements or monitoring in the field.

Frequency domain reflectometry (FDR) uses an oscillating circuit connected to a sensing probe. In the essay of Skierucha and Wilczek, (2010). A FDR Sensor for Measuring Complex Soil Dielectric Permittivity in the 10-500 MHz Frequency Range. Sensors, 10(4), 3314-3329.), they revealed two configurations of FDR probes, impedance sensors and capacitive probes (or fringe capacitive sensors). In an impedance sensor, an oscillator transmits an electrical signal to the waveguide, where the amplitude and phase difference between the output wave and return wave frequency are measured to determine the dielectric permittivity. In capacitance measurements, the conductors of the probe complete an oscillator circuit with the frequency determined by the dielectric permittivity. A frequency domain reflectometer or frequency domain sensor actually uses a single frequency rather than a frequency range for measurement. For low-frequency measurement, the analysis method is based on circuit analysis to obtain the dielectric spectrum, whereas for high-frequency measurement, the corresponding dielectric spectrum is derived based on wave propagation theory.

In the essay of Topp et al., 1980 (Topp, G C, Davis, J L, & Annan, A P (1980). Electromagnetic determination of soil water content: Measurements in coaxial transmission lines. Water Resources Research, 16(3), 574-582.), the conventional travel time based TDR analysis only measures the single-valued apparent dielectric constant with no clear indications of effective frequency.

Regarding spectral analysis of TDR measurements, time-domain dielectric spectroscopy (TDS/TDDS) is based on transmission line theory, and almost every TDS method requires the use of TDR instrument to record incident pulses and reflected pulses in order to extract necessary information for subsequent analysis. The scattering function (in the frequency domain) of the sensing waveguide can be theoretically derived and experimentally measured by spectral analysis of the TDR signal. Fellner-Feldegg (1969) (Fellner-Feldegg, H. (1969). Measurement of dielectrics in the time domain. The Journal of Physical Chemistry, 73(3), 616-623.) and Nicolson and Ross (1970) (Nicolson, A M, & Ross, G F (1970). Measurement of the Intrinsic Properties of Materials by Time-Domain Techniques. IEEE Transactions on Instrumentation and Measurement, 19(4), 377-382.) first demonstrated that theory-based TDS is feasible. They used the scattering function and the transmission coefficients from the time-domain signal to measure the CDP of the material by parameter estimation of the transmission line theory. Fellner-Feldegg, H. (1972) (Fellner-Feldegg, H. (1972). Thin-sample method for the measurement of permeability, permittivity, and conductivity in the frequency and time domain. The Journal of Physical Chemistry, 76 (15), 2116-2122.), Clark et al. (1974) (Clark, A H, Quickenden, P A, & Suggett, A. (1974). Multiple reflection time domain spectroscopy. Application to dielectric relaxation properties of aqueous systems in the time range to 10-10 to 10-4 s. J. Chem. Soc., Faraday Trans. 2, 70(0), 1847-1862.) and van Gernert & Suggett (1975) (van Gernert, M J C, & Suggett, A. (1975). Multiple reflection time domain spectroscopy. II. A lumped element approach leading to an analytical solution for the complex permittivity. The Journal of Chemical Physics, 62(7), 2720-2726.) et al, later considered the multiple reflections of time-domain signals in their TDS formulation, through a thin sample (cell) method or lumped-element model method to further improve the estimation accuracy of CDP of material.

Nevertheless, there is still a need to accurately determine the source function (i.e., the input from the signal generator) to implement these methods. The source function is difficult to determine accurately and may vary with operating temperature. In addition, the derivation of the scattering function assumes that the guiding transmission line before the sensing waveguide has no impedance mismatch and resistive loss, which is difficult to be achieved in practice.

In the essay of Cole, 1975 (Cole, R H (1975). Evaluation of dielectric behavior by time domain spectroscopy. II. Complex permittivity. The Journal of Physical Chemistry, 79(14), 1469-1474.), 1983 (Cole, R H (1983). Bridge Sampling Methods for Admittance Measurements from 500 kHz to 5 GHz. IEEE Transactions on Instrumentation and Measurement, 32(1), 42-47.), another TDS-based full waveform inversion, is formulated by taking the complex admittance with respect to v(t) of the complete waveform, which considers all reflections to estimate CDP. They adopted a coaxial-line bridge arrangement to measure unknown admittances compared to standard materials over a broad spectrum with pulsed or sinusoidal excitation. They stated that the propagation effects up to GHz and all residual reflections are fully accounted for in their formulations without the need for a detailed analysis. However, in this approach, different CDP ranges require different sample container designs and model-based inversion. TDS using the lumped capacitance method was improved using the total difference method (Y. Feldman et al., 1996 (Feldman, Y., Andrianov, A., Polygalov, E., Ermolina, I., Romanychev, G., Zuev, Y., & Milgotin, B. (1996). Time domain dielectric spectroscopy: An advanced measuring system. Review of Scientific Instruments, 67(9), 3208-3216.); Y D Feldman et al. Man, 1978 (Feldman, Y D, Goncharov, V A, Zuev, Y F, & Valitov, V M (1978). Time domain treatment of TDS data for the lumped-capacitance method. Chemical Physics Letters, 58(2), 304-306.) and Multi-Window Non-Uniform Sampling (Hager, 1994) (Hager, N E (1994). Broadband time-domain-reflectometry dielectric spectroscopy using variable-time-scale sampling. Review of Scientific Instruments, 65(4), 887-891.), pushing the effective measurement frequency up to 5 orders of magnitude. This method treats the sample cell as an effective capacitor in the formulation, but its measurement accuracy in the high frequency range may be poor, especially in polar dielectrics (Y. Feldman et al., 1996).

TDS-based total reflection method (Berberian, 1993). Time domain reflectometry: Bilinear corrections and extending the range of analysis beyond the quarter and half wavelength conditions. Journal of Molecular Liquids, 56, 1-18.); Clark et al., 1974). Using a similar transmission line setup, the reflection r(t) is obtained from the sample cell with MUT and compared to a reference reflection with known conditions (such as open circuit, short circuit, or known load conditions). This method is also known as bilinear calibration, which can prevent effects due to non-ideal conditions within the transmission line. Nonetheless, this method still requires several measurements to fully capture the required signals (such as source functions, reflected signals from loads, open/shorted signals) for subsequent analysis. The measurement performance of this method will be highly dependent on the signal integrity of the reference signal of the MUT, and will require re-calibration if the source function changes.

In 2017, Lin et al. (2017) (Lin, C.-P., Ngui, Y J, & Lin, C.-H. (2017). A novel TDR signal processing technique for measuring apparent dielectric spectrum. Measurement Science and Technology, 28(1), 015501.) proposed a phase velocity analysis (PVA) method for extracting apparent permittivity from TDR signals without knowing the input function and calibrating the leading transmission line. It extracts the first and second reflection signals to analyze the phase velocity spectrum of the round-trip propagation within the sensing waveguide. PVA analysis yields frequency-dependent apparent permittivity spectrum, which is the combined effect of the real and imaginary parts of the CDP. The measurable bandwidth of this method is limited by the length of the sensing part and the dielectric permittivity of the MUT.

With the capability of separating the contributions of different reflection components in the scattering function, in 2018, in the essay of Lin et al. (Lin, C.-P., Ngui, Y J, & Lin, C.-H. (2018). Multiple Reflection Analysis of TDR Signal for Complex Dielectric Spectroscopy. IEEE Transactions on Instrumentation and Measurement, 67(11), 2649-2661.) and 2019 Ngui et al. (Ngui, Y J, Lin, C.-P., & Wu, T.-J. (2019). Dielectric Spectroscopy Using Dual Reflection Analysis of TDR Signals. Sensors, 19(6), 1299.), MRA and DRA are proposed respectively to measure the CDP spectrum by extracting the spectral analysis of the reflection components. This was an early attempt at the self-referencing concept, in which the sum of the second or remaining reflections in the frequency domain is divided by the first reflection to obtain the spectral ratio. Thereby eliminating the effects of the source function and reducing the effects of impedance mismatches in the leading transmission line. The frequency range in which DRA and MRA perform well depends on whether their reflection components are well extracted or completely separated in the frequency domain. The high resistivity loss in the leading transmission line and the high dielectric dispersion of MUT make it impossible to completely separate the first reflected component from the rest, reducing the measurable bandwidth of the CDP.

SUMMARY OF THE INVENTION

In view of the above limitations, a fast, robust, flexible and convenient dielectric spectroscopy technique is proposed in the present invention to measure the complex dielectric permittivity (CDP) spectrum of materials to be more accurate in a wider frequency range.

In view of this, a fast, robust, flexible and convenient dielectric spectrum technique is proposed in the present invention based on the self-referencing time domain reflectometry (TDR) technique to more accurately measure the CDP of materials in a wider frequency range. Instead of using the first reflection from the sensing section as the self-referenced signal, a new stable self-referenced signal is induced by a known impedance mismatch section in an artificially induced manner. The technique of the present invention analyzes and obtains the complex dielectric spectrum by decoupling the self-referencing reflection signal and all other signals affected by the sensing section, so the technique is referred hereinafter to as Reflection Decoupled Analysis (RDA).

According to the above framework, a measuring device for complex dielectric material using multiple reflections from time-domain signals is disclosed. The device includes an electromagnetic wave generating/receiving unit, a transmission line, an impedance mismatch section, a first interface and a sensing section. The electromagnetic wave generating/receiving unit is configured to generate an electromagnetic wave signal. The transmission line has a first characteristic impedance and is connected to the electromagnetic wave generating/receiving unit. The impedance mismatch section has a second characteristic impedance. The first interface is formed between the transmission line and the impedance mismatch section, wherein the electromagnetic wave signal is transmitted from the transmission line to the first interface to form a first reflection signal and a first transmitted signal. The sensing section is configured to measure a material under test (MUT) with unknown complex dielectric permittivity (CDP) spectrum, wherein a second interface is formed between the impedance mismatch section and the sensing section. The first transmitted signal is transmitted from the impedance mismatch section to the second interface, and reflected through the second interface to form remaining subsequent $k^{th}$ reflection signals, where $k \geq 2$. The electromagnetic wave generating/receiving unit receives the first reflection signal and the remaining subsequent $k^{th}$ reflection signals ($k \geq 2$) to measure the CDP spectrum of the MUT.

In accordance with one aspect of the present invention, a method for measuring multiple reflection from time-domain signals of a material under test (MUT) is disclosed. The method includes the following steps of: providing a self-referencing waveguide section having a front end, a back end and a sensing waveguide section connected to the back end. Generating an electromagnetic wave signal. Transmitting the generated electromagnetic wave signal in a first medium with a first characteristic impedance. When the electromagnetic wave signal is transmitted from the first medium to the front end, a first reflection signal and a first transmitted signal are departed from the front end, wherein the self-referencing waveguide section has a second characteristic impedance. Under a first condition that the first transmitted signal is transmitted from the front end to the sensing waveguide section, the remaining subsequent $k^{th}$ reflection signals ($k \geq 2$) reflected through the sensing waveguide section and the back end. Under a second condition that the first reflection signal is received in a first time window and the remaining subsequent $k^{th}$ reflection signals ($k \geq 2$) are received in a second time window, measuring the complex dielectric permittivity of the MUT.

In accordance with one aspect of the present invention, a device for measuring the complex dielectric permittivity (CDP) of a material under test (MUT) is disclosed. The device includes an electromagnetic wave generating/receiving unit, a transmission line, a self-referencing waveguide section and a sensing waveguide section. The electromagnetic wave generating/receiving unit is configured to generate an electromagnetic wave signal. The transmission line has a first characteristic impedance and transmits the electromagnetic wave signal. The self-referencing waveguide section has a second characteristic impedance, and includes a front end and a back end, wherein a first reflection signal is reflected from the front end. The sensing waveguide section is connected to the back end, and the remaining subsequent $k^{th}$ reflection signals ($k \geq 2$) are reflected from the back end, wherein the electromagnetic wave generating/receiving unit receives the first reflection signal and the remaining subsequent $k^{th}$ reflection signals ($k \geq 2$) to measure the CDP of the MUT.

The advantages of the present invention are listed as follows:

1. The technique of the present invention inherits all the advantages of the traditional TDR dielectric spectroscopy, and uses more economical TDR instrument, enabling highly efficient measurements in time domain without requiring multiple frequency sweeps.

2. This self-referencing technique eliminates the need for input functions that are difficult to measured accurately, and are immune to changes in the input function (e.g., due to the temperature).

3. This self-referencing technique eliminates the need for calibrating the leading transmission lines. The system parameters required to be calibrated are simple, which are simply the geometric factor and the length of the probe. Its calibration can be performed easily once and for all by using a standard material with a well-known dielectric spectrum, such as distilled water or alcohol.

4. Since the electrical characteristics and the length of the self-referencing waveguide section are fixed, the self-referencing technique can use two fixed selections of time windows, which contain the first reflected signal and the remaining subsequent $k^{th}$ reflected signals ($k \geq 2$) respectively, so as to separate the reflected signals. This time window selection is not affected by the length, the geometry of the sensing waveguide section and the MUT.

5. Therefore, the probe design is more flexible in this self-referencing technique. The effects of the leading transmission line and the probe mismatch are largely eliminated. Different types of sensing waveguides can be designed for different types of materials and measurement conditions. High spatial resolution can be achieved by using ultrashort sensing sections. Current conventional CDP measurement system does not allow the flexible customization of the probe design according to the measurement material or different environment, wherein the preparation of the measurement sample always needs to accommodate to the limitations of the specially designed probe of the measurement system. On the contrary, the technique of the present invention allows the customization of the probe design (such as the sensing type and geometric dimensions). The present invention is applicable to probes of any size and configuration.

6. Combining the above features, this self-referencing technique enables field measurements or monitoring of the dielectric spectrum in natural or engineered environments.

The above objectives and advantages of the present invention will become more readily apparent to those ordinarily skilled in the art after reviewing the following detailed descriptions and accompanying drawings, in which:

DETAILED DESCRIPTION OF THE PREFERRED EMBODIMENTS

The present invention will now be described more specifically with reference to the following embodiments. It is noted that the following descriptions of preferred embodiments of this invention are presented herein for the purposes of illustration and description only; they are not intended to be exhaustive or to be limited to the precise form disclosed.

Figure 1:
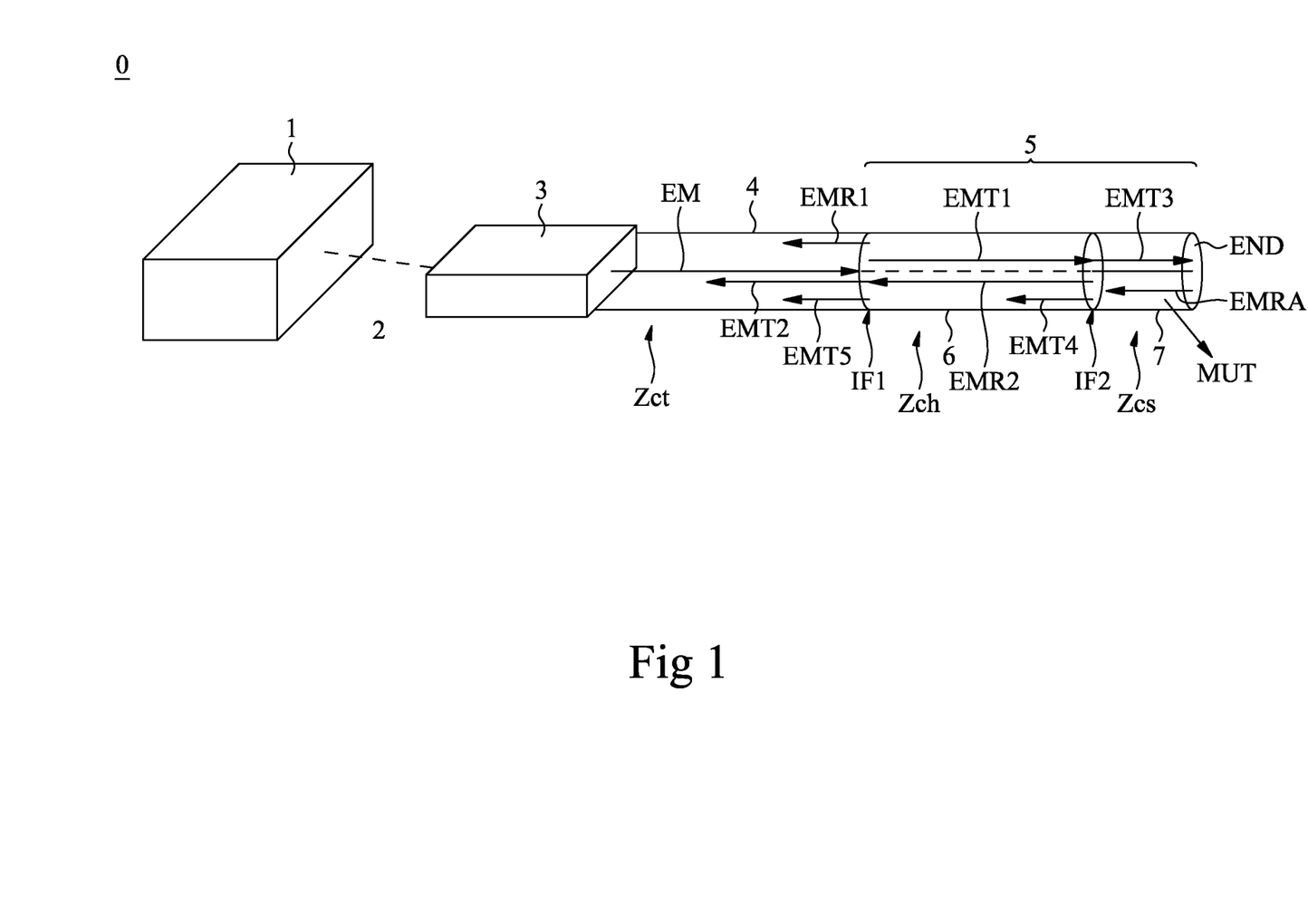
FIG. 1 is a schematic diagram showing a measurement device for multiple reflections of time-domain signal of a complex dielectric material according to a preferred embodiment of the present disclosure.

Please refer to FIG. 1, which is a schematic diagram showing a measurement device 0 for time-domain signals of a complex dielectric according to a preferred embodiment of the present disclosure. The measurement device 0 includes an electromagnetic wave generating/receiving unit 3, a transmission line 4, an impedance mismatched section 6, a first interface IF1, a sensing section 7 and a second interface IF2. The electromagnetic wave generating/receiving unit 3 is configured to generate an electromagnetic wave signal EM. The transmission line 4 has a first characteristic impedance Zct, transmits the electromagnetic wave signal EM, and is connected to the electromagnetic wave generating/receiving unit 3. The impedance mismatched section 6 has a second characteristic impedance Zch. The first interface IF1 is formed between the transmission line 4 and the impedance mismatch section 6, wherein the electromagnetic wave signal EM is transmitted from the transmission line 4 to the first interface IF1 to form a first reflection signal EMR1 and a first transmitted signal EMT1. The sensing section 7 is configured to measure a material-under-test (MUT) with a complex dielectric spectrum, wherein the second interface IF2 is formed between the impedance mismatch section 6 and the sensing section 7. The first transmitted signal EMT1 is transmitted from the impedance mismatch section 6 to the second interface IF2, and is reflected through the second interface IF2 to form a k-th reflected signal EMR2, wherein k≥2. The electromagnetic wave generating/receiving unit 3 receives the first reflection signal EMR1 and the remaining subsequent reflection signals (k≥2) EMT2 to measure the complex dielectric spectrum E (f) of the MUT.

The measurement device 0 in FIG. 1 is suitable to serve as the measurement device of the Reflection Decoupled Analysis (RDA) method, and the measurement device 0 further includes a data recorder 1 and a communication cable 2. The electromagnetic wave generating/receiving unit 3 can be a time-domain reflectometry (TDR) device, and the transmission line 4 can be a coaxial cable. For the implementation of the RDA, the self-referencing sensing waveguide 5 includes a self-referencing section (e.g., an impedance mismatch section 6) and a sensing section 7, as shown in FIG. 1. The self-referencing section is basically an impedance mismatch section 6 of a coaxial waveguide or multi-rod waveguide having a characteristic impedance being different from that of the transmission line 4. The sensing section 7 may be in the form of a coaxial probe or a multi-rod probe. The terminal END of the sensing section 7 is in an open-ended state, and all electromagnetic wave signals can be totally reflected at the open terminal END. In another embodiment, the terminal END of the sensing section 7 is in a closed circuit state, and the reflection coefficient at the terminal END becomes equal to −1 (the negative total reflection).

The measurement process is performed by immersing a coaxial probe into the MUT or inserting a multi-rod probe into the MUT. The data recorder 1 sends an instruction to the electromagnetic wave generating/receiving unit 3 (being a TDR instrument), and sends the electromagnetic wave signal EM to the self-referencing sensing waveguide 5 along the transmission line 4 (coaxial cable), where digitized data is transmitted through the communication cable 2. The reflection signals are recorded by the TDR instrument.

As shown in FIG. 1, the input signal, that is, the electromagnetic wave signal EM generated by the electromagnetic wave generating/receiving unit 3 is denoted by X, the transmission effect of the electromagnetic wave signal EM in the emission path of the transmission line 4 is denoted by F, and the reception of the electromagnetic wave signal EM in the receiving path of the transmission line 4 is denoted by B. The relationship between the electromagnetic wave signal EM and the first reflection signal EMR1 is represented by a reflection coefficient ρ1. The transmission effect F is formed when the electromagnetic wave signal EM is transmitted in the emission path in the transmission line 4. The electromagnetic wave signal EM passes through the first interface IF1, and forms the reflection effect after the reflection of the first interface IF1. The transmission effect B is formed when the electromagnetic wave signal EM is transmitted in the receiving path in the transmission line 4. After the transmission effect B is formed, the signal received by the electromagnetic wave generating/receiving unit 3 is represented by R1, in which R1=X·F·ρ1(Zch, Zct)·B (Equation 1), where the ρ1 function is the reflection coefficient at the first interface IF1, $$\rho 1 = \frac{Zch - Zct}{Zch + Zct}, \quad \text{(Equation 2)}$$

the transmission coefficient of the emission path at the same interface position can be expressed as (1+ρ1), and the transmission coefficient of the receiving path is equal to (1−ρ1).

Continuing from the above, when the electromagnetic wave signal EM is transmitted through the first interface IF1, there is a first transmitted signal EMT1 in addition to the first reflection signal EMR1. The transmission effects of the emission path and the receiving path of the self-referencing section (e.g., the matching section 6) are represented by MSF and MSB respectively; and the relationship between the first transmitted signal EMT1 and the remaining subsequent $k^{th}$ reflection signals (k≥2) EMR2 is represented by a second reflection coefficient ρ2.

The transmission effect F is formed when the electromagnetic signal EM is transmitted in the emission path of the transmission line 4. A transmission effect is formed after the electromagnetic signal EM passes through the first interface IF1. The transmission effect MSF is formed when the electromagnetic signal EM is transmitted through the emission path in the impedance mismatch section 6. A reflection effect is formed after the electromagnetic signal EM is reflected by the second interface IF2. The transmission effect MSB is formed after the electromagnetic signal EM passes through the receiving path in the impedance mismatch section 6. The transmission effect B is formed after the electromagnetic signal EM passes through the receiving path in the transmission line 4. After the transmission effect B is formed, the electromagnetic wave generating/receiving unit 3 receives the signal. The signal is represented by R2, and then R2=X·F·[1+ρ$_1$(Zch,Zct)]·HMS·ρ2·[1−ρ$_1$(Zch,Zct)]·B (Equation 3), wherein Zcs is a third characteristic impedance of the sensing section 7 including the MUT; and the function ρ2 is the reflection coefficient at the second interface IF2, which includes all effects from the sensing section 7. function ρ2 is critical to the RDA method and to be further elaborated in the next two paragraphs.

After the first to second reflections or transmissions of the electromagnetic wave signal EM at the first interface IF1, the second interface IF2, and the open or closed circuited terminal END, the subsequent reflected or transmitted energy will attenuate until it disappears; and summed signals received by the electromagnetic wave generating/receiving unit 3 will also converge eventually, but the major reflection signals that can affect the dielectric spectrum measurement is the first one to two reflected signals or the transmitted signals.

Since the analytical formulation of reflection signals and multiple reflections for the electromagnetic wave signal EM transmitted after the second interface IF2 is very difficult to be derived by the ray tracing method, the present invention adopts the input impedance method for reflection signals after IF2. The second interface IF2 of the sensing section 7 has a first effect; the length of the sensing section 7 and the complex dielectric spectrum εMUT(f) of the MUT have a second effect; and the open end terminal END has a third effect. The first, the second and the third effects are integrated into a characteristic boundary effect at the second interface IF2 through the input impedance method, and are combined into the ρ2 function of Equation 3, so that R2=X·F·[1−ρ$_1^2$(Zch, Zct)]·HMS·ρ2(Zcs,Zch,γ$_{SS}$,L$_{SS}$)·B (Equation 4). The second reflection coefficient ρ2 represents the effect of integrating these three effects on the feature boundary, is expressed as $$\rho 2 = \frac{Z_{cs} \cdot \coth(\gamma_{SS} L_{SS}) - Z_{ch}}{Z_{cs} \cdot \coth(\gamma_{SS} L_{SS}) + Z_{ch}}, \quad \text{(Equation 5)}$$

wherein γ$_{SS}$ is the wave propagation function of the sensing section 7, and L$_{SS}$ represents the length of the sensing section 7.

Owing to the input impedance method, the third transmitted signal EMT3 at the second interface IF2 and all the effects formed by the total reflection signal EMRA returning to the second interface IF2 after the third transmitted signal EMT3 reaches the terminal END, are all included in the second reflection coefficient ρ2 of the second interface IF2. The subsequent multiple reflection signals only need to be deduced to the second interface IF2, whereas all the effects of the second interface IF2 and even the third interface IF3 are integrated into the second reflection coefficient ρ2. The fourth transmitted signal EMT4 is formed through the transmission of the second interface IF2; the fifth transmitted signal EMT5 is formed through the transmission of the first interface IF1 (being the same as the transmission effect B of the receiving path in the transmission line 4); and the third reflection signal received by the electromagnetic wave generating/receiving unit 3 is represented by R3, R$_3$=X·F·B·[H$_{MS}$(1−ρ$_1^2$)(ρ$_2$)]·[−ρ$_1$ρ$_2$H$_{MS}$] (Equation 6). Similar trajectory for other multiple reflections can be traced with this derivation method, whereas the signals that are reflected and transmitted back and forth between the first interface IF1 and the second interface IF2, until they fully attenuate and disappear, can be represented by R$_k$, wherein R$_k$=X·F·B·[H$_{MS}$(1−ρ$_1^2$)(ρ$_2$)]·[−ρ$_1$ρ$_2$H$_{MS}$]$^{(k-2)}$ (Equation 7), for k=2, 3, . . . , n.

The sum of R2~Rn and the sum of R1~Rn are obtained from Equation 7 through geometric series summation, which are expressed as R$_{remaining}$ and R$_{all}$ respectively as follows, wherein $$R_{remaining} = X \cdot F \cdot B \cdot [H_{MS}(1 - \rho_1^2)(\rho_2)] \cdot \frac{1}{1 + \rho_1 \rho_2 H_{MS}}, \quad \text{(Equation 8)}$$

$$\text{and } R_{all} = X \cdot F \cdot B \cdot \left[\rho_1 + \frac{H_{MS}(1 - \rho_1^2)\rho_2}{1 + \rho_1 \rho_2 H_{MS}}\right]. \quad \text{(Equation 9)}$$

A self-referencing technique (or decoupling the received electromagnetic wave signal) can eliminate the effect of input function by comparing Equation 1, Equation 8, and Equation 9. For example, selecting two among the three equations to make a division between the two, so as to obtain the spectral reflection decoupled ratio (RDR), in order to eliminate the common factors of the input signal X, the transmission effect F of the emission path of the electromagnetic signal EM in the transmission line 4, and the transmission effect B of the receiving path of the electromagnetic signal EM in the transmission line 4. For example, dividing Equation 8 by Equation 1 to obtain $$RDR_1 = \frac{R_{remaining}}{R_1} = \frac{\rho_2 H_{MS}(1 - \rho_1^2)}{\rho_1(1 + \rho_1 \rho_2 H_{MS})}. \quad \text{(Equation 10)}$$

It can be clearly seen that the input signal X and the effects F and B of the electromagnetic wave signal EM on the transmission line 4 have been decoupled and eliminated through this self-referencing technique.

The input signal X and the effects F and B of the electromagnetic wave signal EM on the transmission line 4 have been eliminated. In addition, the system parameters, such as ρ1(Zch, Zct) and HMS, can be designed or appropriately selected, so that the time window of the signal received by the electromagnetic wave generating/receiving unit 3 may not be affected by the type of MUT, thereby not requiring the time window to be adjusted necessarily every time when different types of MUTs are measured, especially when the target MUT has significant dielectric dispersion. Moreover, if there is no impedance mismatch section 6, it is possible that the second transmitted signal EMT2 has been received by the electromagnetic wave generating/receiving unit 3 before the first reflection signal EMR1 has been completely developed. On the contrary, if there is an impedance mismatch section segment 6, this situation can be completely avoided, and the lengths of the transmission line 4 and the self-referencing sensing waveguide 5 can be designed to be very short.

Figure 2A:
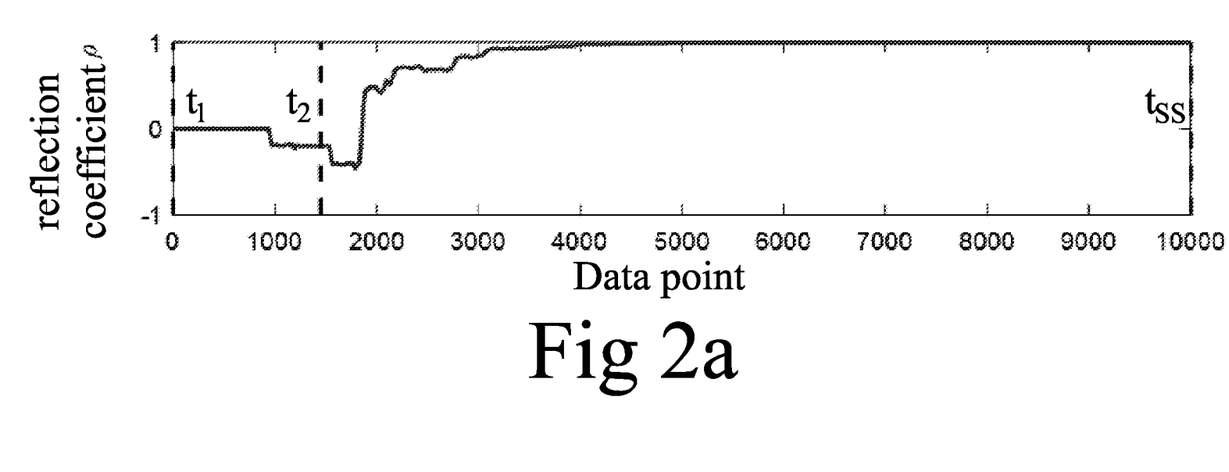
FIG. 2a is a schematic diagram showing a waveform diagram of a signal received by the electromagnetic wave generating/receiving unit according to a preferred embodiment of the present invention.

Please refer to FIG. 2a, which is a waveform diagram showing a signal received by the electromagnetic wave generating/receiving unit 3 according to a preferred embodiment of the present invention. The horizontal axis represents time, in data points, whereas the vertical axis represents the reflection coefficient ρ, which is defined as the ratio between the input signal X and the total received signal. Please refer to FIG. 2b, which is a waveform diagram showing a differentiated signal corresponding to the signal shown in FIG. 2a according to the preferred embodiment of the present invention. For the RDA measurement method, a single measurement recording is divided into two parts, the first part from the impedance mismatch section 6, whereas the second part is the rest of the multiple reflection signals. The first reflection signal EMR1 of the impedance mismatched section 6 is used as a self-referencing signal for RDA dielectric spectrum analysis. As shown in FIG. 2a, the first reflection signal EMR1 coining from the impedance block 6 can be acquired by the time window between t1 and t2, wherein t1 is the time before the first reflection signal EMR1 is reflected from the first interface IF1 between the transmission line 4 and the impedance mismatch section 6; and t2 is the travel time close to but before the fourth transmitted signal EMT4 is reflected from the second interface IF2 between the impedance mismatch section 6 and the sensing section 7. The remaining multiple reflection signals can be acquired by a time window between t2 and $t_{SS}$, wherein $t_{SS}$ is the time long enough to reach the steady state of the signal under test.

In Equation 10, only the transmission effects MSF and MSB of the emission path and the receiving path of the electromagnetic wave EM in the impedance mismatch section of the impedance block, and the reflection effect $\rho2(Zcs, Zch, \gamma\_SS, L\_SS)$ at the second interface IF2 are left to be solved. The transmission effects MSF and MSB of the emission path and the receiving path of the electromagnetic wave EM in the impedance mismatch section are system parameters, which can be appropriately selected or designed to correspond to (or to be associated with) a fixed time window t1~t2. The reflection effect $\rho2(Zcs, Zch, \gamma_{SS}, L_{SS})$ and the transmission effect $[1+\rho2(Zcs, Zch, \gamma_{SS}, L_{SS})]$ at the second interface IF2 can also be selected or designed to correspond to (or to be associated with) the time window t2~$t_{SS}$. In addition, the waveforms of different signals can correspond to (or be associated with) the complex dielectric spectrum $\epsilon(f)$ of different MUTs (f), which can detect which substance the MUT belongs to.

In FIG. 2a, the signal received by the electromagnetic wave generating/receiving unit 3 in the time windows t1~t2 and t2~$t_{SS}$ need to be converted into a signal in the frequency domain. Taking the acetone as an example, its RDA analysis process is described as follows:

1. The electromagnetic wave generating/receiving device 3 is used to record the time domain signal, as shown in FIG. 2a.

Figure 2B:
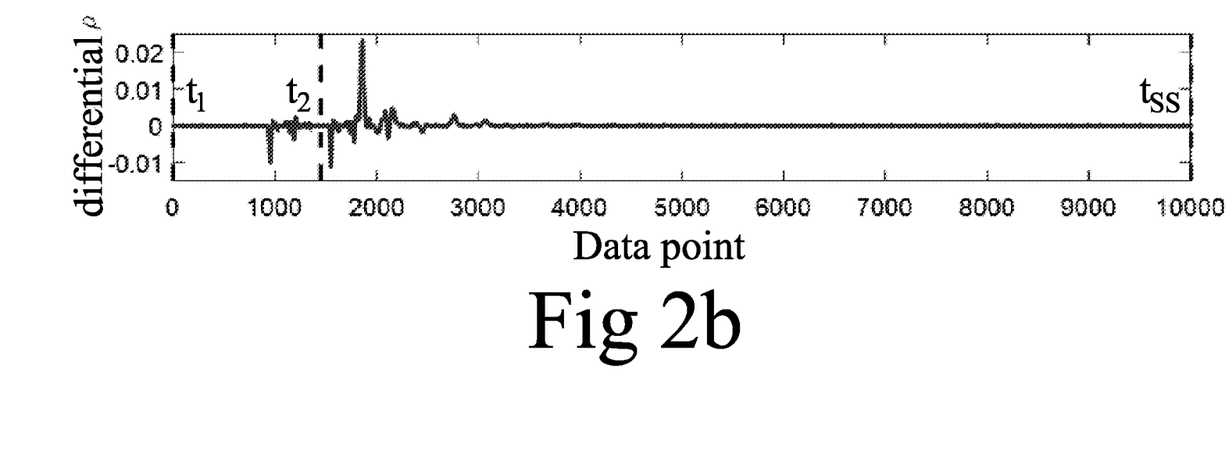
FIG. 2b is a schematic diagram showing a waveform diagram corresponding to the differential signal in FIG. 2a according to the preferred embodiment of the present invention.

2. The electromagnetic wave generating/receiving device 3 usually emits a step pulse. In this case, the step impulse response is differentiated over time to convert it to a short impulse response, as shown in FIG. 2b.

3. The time domain signals are acquired from t1 and t2 as the reference signal r1B, while the signal formed from t2 to $t_{SS}$ is used as $r_{remaining}$, or the signal formed from t1 to $t_{SS}$ is used as $r_{all}$.

4. A window function and a low pass filter are applied to the acquired signals $r_1$, $r_{remaining}$ or $r_{all}$ to suppress random noise.

5. The acquired signal should be zero-padded to achieve the desired frequency resolution.

6. The signal is converted into the frequency domain by using Fast Fourier Transform (FFT) to obtain $r_1$, $r_{remaining}$ or $r_{all}$, respectively.

7. The spectral RDR ratio of the acquired signal frequency is calculated with any of the following six combinations: $R_{remaining}/R_1$, $R_{all}/R_{remaining}$, $R_{all}/R_1$, $R_1/R_{remaining}$, $R_{remaining}/R_{all}$, $R_{all}/R_{remaining}$.

8. An optimization algorithm is used to match the measured RDR ratio with the theoretical value, where the experimental spectral ratios for each frequency are inverted to CDP, and an example measurement is shown in FIG. 3a.

Figure 3A:
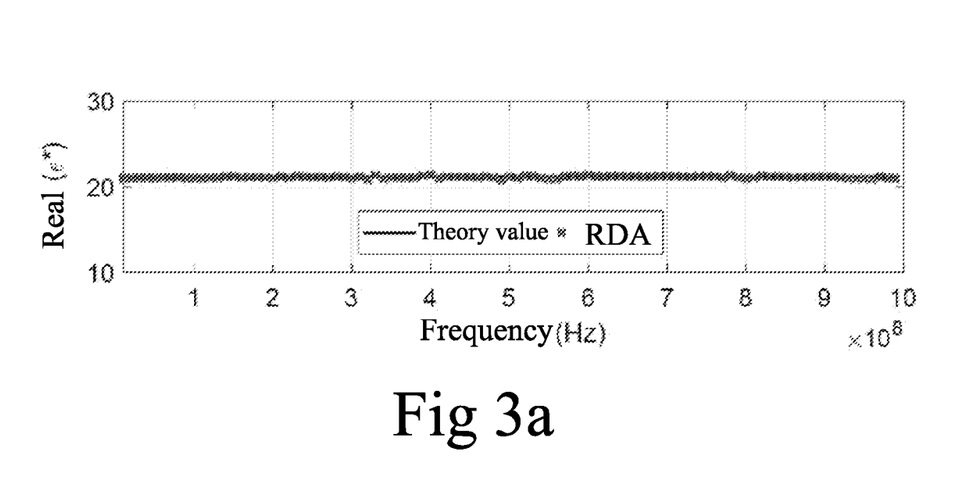
FIG. 3a is a schematic diagram showing the real part of the CDP spectrum $\varepsilon(f)$ of the MUT according to a preferred embodiment of the present invention.
Figure 3B:
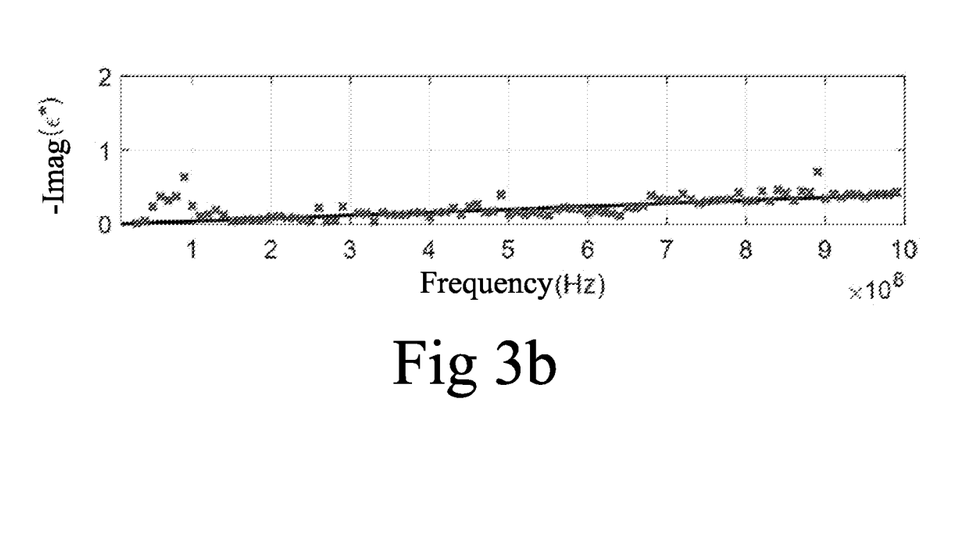
FIG. 3b is a schematic diagram showing the imaginary part of the CDP spectrum $\varepsilon(f)$ of the MUT according to the preferred embodiment of the present invention.

Please refer to FIG. 3a, which is a schematic diagram showing the real part of the CDP spectrum of the MUT according to a preferred embodiment of the present invention. The horizontal axis represents the frequency, whereas the vertical axis represents the real part of the CDP spectrum, which is called the permittivity. Please refer to FIG. 3b, which is a schematic diagram showing the imaginary part of the CDP spectrum of the MUT according to the preferred embodiment of the present invention. The horizontal axis represents the frequency, whereas the vertical axis represents the imaginary part of the CDP spectrum, which is called the loss factor. The solid lines shown in FIGS. 3a and 3b represent theoretical values, whereas the sign of x represents the experimental values measured using the RDA method for the measurement device 0 having the impedance mismatch section 6.

As shown above, the effects formed from the previous sections and the resulting input can be eliminated by the self-referencing RDA spectral ratio (RDR). In RDA, the time window selection for $r_{MS}$, $r_{remaining}$, and $r_{all}$ is static, which means that the time window selection is independent of the MUT in the sensing section, so this measurement setup only require a one-time system calibration that is quick and easy. Since the time window selection point does not lie within the reflection signal EMRA formed after the impedance mismatched section 6, the length required for the sensing section 7 can be very small. Calibration of the parameters (such as the geometric impedance and the section length) of the transmission line 4 can be performed by using standard materials with well-known dielectric spectra (such as distilled water, methanol, ethanol, isopropanol, butanol, or acetone), in which the impedance mismatch sections 6 and the sensing section 7 can be easily tested. For MUTs having high temperature dependency, temperature readings obtained from a temperature sensor (not shown) can be used to adjust the measured complex dielectric spectrum accordingly.

The use of a portable data recorder 1 and an electromagnetic wave generating/receiving unit 3, such as a TDR device, is allowed in the present invention, and is capable of fast, reliable, and convenient implementations of the dielectric spectrum over a wider frequency range within the TDR bandwidth. Since this technique only requires the acquisition of time-domain signals, the time required for acquisition and analysis is greatly reduced, and the prior knowledge of the input function is not required, which greatly reduces measurement errors caused by inconsistent signal generators, and eliminates the need for frequent system recalibrations. Since the analysis technique in the present invention is based on the reference of the artificially-induced signal by the impedance mismatch section 6, the static time window selection shown in FIG. 2 allows robust measurement and analysis regardless of the measured MUT type. This would further allow the technique to reduce the minimum length required for the sensing segment 7, which would increase the spatial resolution. Thus, the present invention has a high degree of flexibility in probe design, allowing customized probes to be adapted to the measurement sample/environment, rather than being otherwise limited by the type of MUT. The sample measurement results using the standard probe configuration in the present invention are shown in FIG. 3, wherein the accuracy of the measurements from the RDA technique using TDR signals is shown to be highly accurate, which is almost close to the theoretical value.

Figure 4:
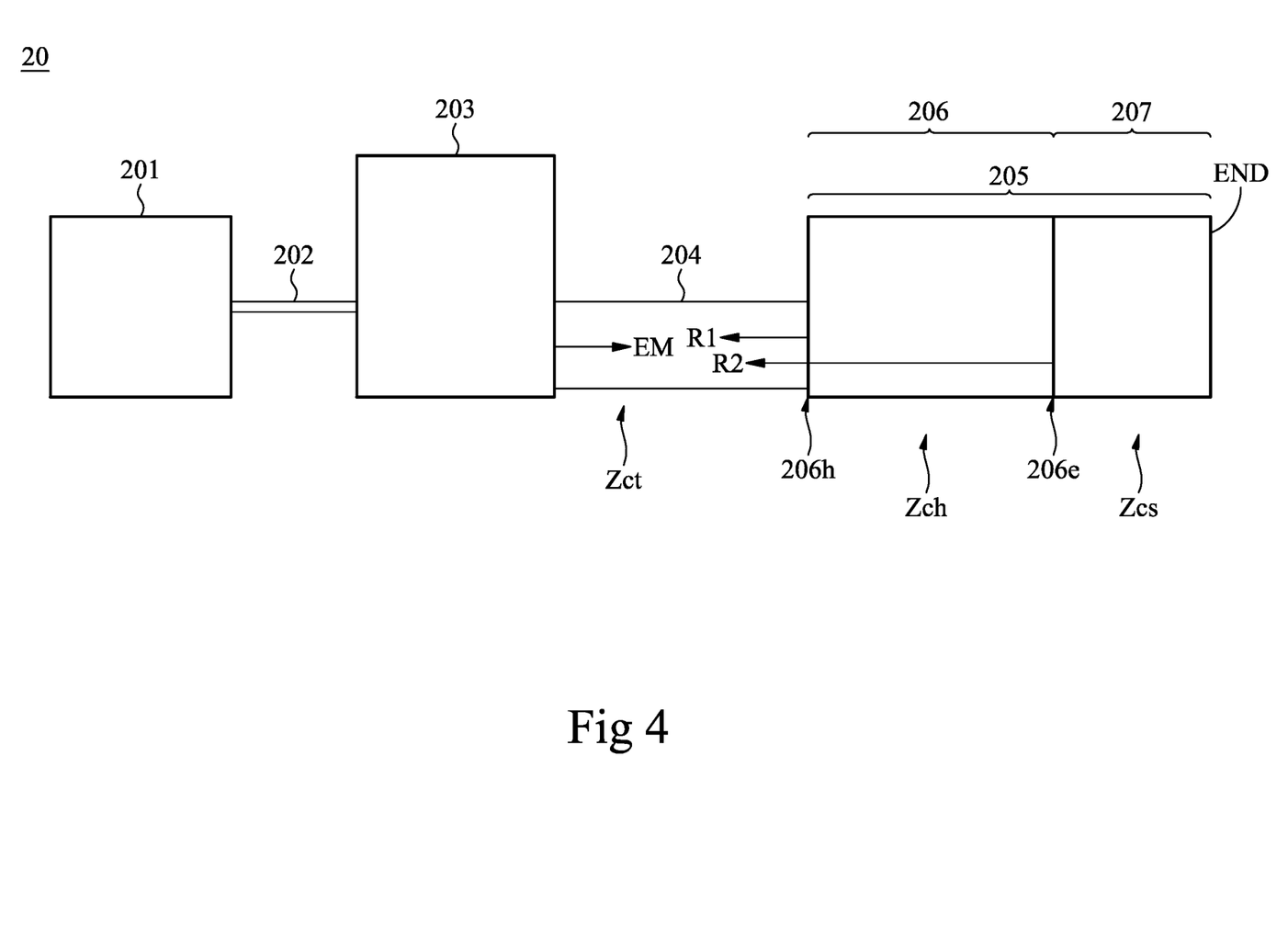
FIG. 4 is a schematic diagram showing a device for measuring the CDP of an MUT according to a preferred embodiment of the present invention.

Summarizing the above, please refer to FIG. 4, which is a schematic diagram showing a device 20 for measuring the CDP of an MUT according to a preferred embodiment of the present invention. The device 20 includes an electromagnetic wave generating/receiving unit 203, a transmission line 204 connected to the electromagnetic wave generating/receiving unit 203, a self-referencing waveguide section 206 connected to the transmission line 204, and a sensing waveguide section 207 connected to the self-referencing waveguide section 206. The electromagnetic wave generating/receiving unit 203 is configured to generate an electromagnetic wave signal EM. The transmission line 204 has a first characteristic impedance Zct and transmits the electromagnetic wave signal EM. The self-referencing waveguide section 206 has a second characteristic impedance Zch, and includes a front end 206h and a back end 206e, wherein a first reflection signal R1 is sent from the front end 206h. The sensing waveguide section 207 is connected to the back end 206e, and is configure to send out remaining subsequent reflection signals (k≥2) R2 from the rear end 206e; and the electromagnetic wave generating/receiving unit 3 receives the first reflection signal R1, wherein the electromagnetic wave generating/receiving unit 3 receives the first reflection signal R1 and the remaining subsequent reflection signals (k≥2) R2 to measure the CDP of the MUT.

In any embodiment of the present invention, the self-referencing waveguide section 206 and the sensing waveguide section 207 form a self-referencing sensing waveguide 205; and the electromagnetic wave generating/receiving unit 3 records a time domain signal, and includes a Time Domain Reflectometer (TDR) or a Vector Network Analyzer (VNA). The sensing section 7 or the sensing waveguide section 207 has a terminal END to form a total reflection. The measurement device (0, 20) uses a very short length waveguide (e.g., a self-referencing sensing waveguide (5, 205), a sensing section 7, or a sensing waveguide section 207) for highly spatially resolved point measurements, wherein the measurement device (0, 20) is applied to a high salinity environment. The device (0, 20) further includes a data recorder (1, 201) and a communication cable (2, 202). The communication cable (2, 202) is connected to the electromagnetic wave generating/receiving unit 203 and the data recorder (1, 201).

Please refer to FIG. 1 and FIG. 4. In any embodiment of the present invention, the remaining subsequent reflection signals (k≥2) R2 include all the first and second or more reflection signals transmitted through the front end 206h; and the primary reflection signal R1' (e.g., R1' in Equation 3) refers to a reflection signal EMR2 that transmits through the front end 206h for the first time and is reflected by the back end 206e for the first time, and then transmits through the front end 206h, i.e., a transmitted signal EMT2 of a reflection signal EMR2.

In any embodiment of the present invention, the first reflection signal R1 is detected in a first time window $t_1-t_2$. The remaining $k^{th}$ subsequent reflection signals (k≥2) R2, EMR2, or EMRA are detected in a second time window $t_2-t_{SS}$. The time samples of the first time window $t_1-t_2$ are related to the first characteristic impedance Zct of the transmission line (4, 204) and the second characteristic impedance Zch of the impedance mismatch section (6, 206). The time sampling of the second time window $t_2-t_{SS}$ is related to the length of one of the sensing section 7 and the sensing waveguide 207, and the complex dielectric spectrum ε(f) of the MUT.

In any embodiment of the present invention, the impedance mismatch section (6, 206) includes a uniform material, and dielectric insulating materials or materials having different geometric impedances. The first reflection signal R1 is used as a reference signal and is related to the remaining subsequent reflection signals Rk (k≥2), wherein the first reflection signal R1 is compared with the remaining subsequent reflection signals (k≥2) Rk to remove the source function influence.

In any embodiment of the present invention, the measurement device (0, 20) is a dielectric spectrum analyzer. The dielectric spectrum analyzer is applied to at least one selected from a group consisting of: a suspended sediment concentration (SSC) measurement; an SSC measurement in high salinity environment; and fields requiring dielectric properties or dielectric spectrum measurement including material science, physical chemistry, agri-food industry, environmental engineering, geotechnical engineering, or civil engineering.

Figure 5:
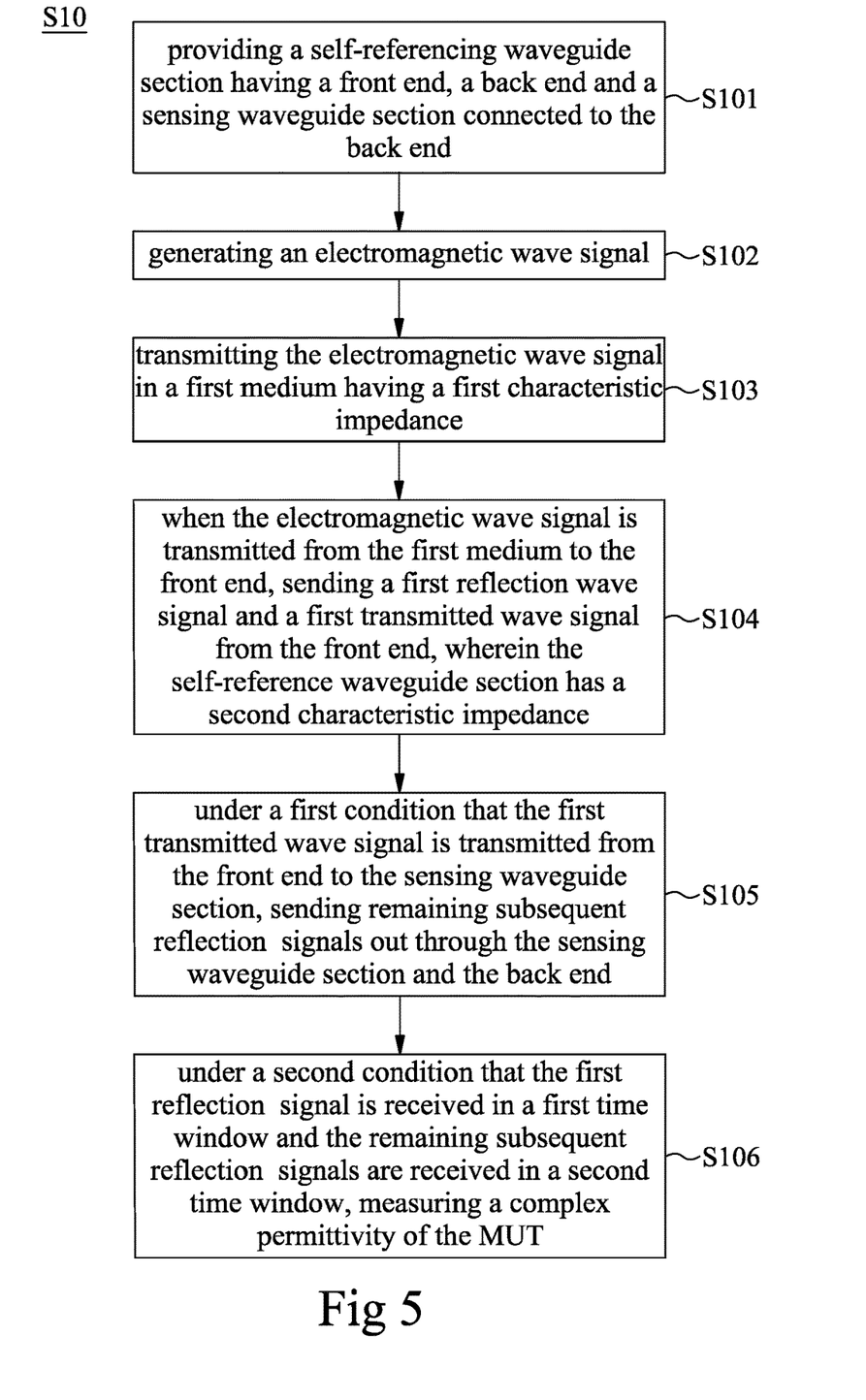
FIG. 5 is a schematic diagram showing a method for measuring the multiple reflections of time-domain signal of an MUT according to a preferred embodiment of the present invention.

Please refer to FIG. 5, which is a schematic diagram showing a method S10 for measuring the multiple reflection of time-domain signals of an MUT according to a preferred embodiment of the present invention. Summarizing the above, the measuring method S10 includes the following steps: Step S101, a self-referencing waveguide section having a front end and a back end and a sensing waveguide section connected to the back end is provided. Step S102, an electromagnetic wave signal is generated. Step S103, the electromagnetic wave signal is transmitted in a first medium having a first characteristic impedance. Step S104, when the electromagnetic wave signal is transmitted from the first medium to the front end, a first reflection signal and a first transmitted signal are sent from the front end, wherein the self-referencing waveguide section has a second characteristic impedance. Step S105, under a first condition that the first transmitted signal is transmitted from the front end to the sensing waveguide section, remaining subsequent reflection signals are sent out through the sensing waveguide section and the back end. Step S106, under a second condition that the first reflection signal is received in a first time window and the remaining subsequent $k^{th}$ reflection signals (k≥2) are received in a second time window, a CDP of the MUT is measured.

In any embodiment of the present invention, a static window selection method for analysis is further included, wherein the static window selection method is in the first time window being independent of the MUT in the sensing waveguide section.

In any embodiment of the present invention, the measuring method S10 further includes the following steps: A fast Fourier transform (FFT) is performed on the signals measured in the first time window $t_1-t_2$, the second time window $t_2-t_{SS}$, and all the time windows $t_1-t_{SS}$. The time-domain signals are respectively converted into a first reflection wave frequency signal R1, a remaining subsequent reflection wave frequency signals $R_{remaining}$ and a total reflection wave frequency signal $R_{all}$. In addition, the sensing waveguide section is filled with the MUT, or the sensing waveguide section is inserted or immersed into the MUT.

In any embodiment of the present invention, the first reflection signal is detected in a first time window having a first sampling duration corresponding to (or associated with) a length and a permittivity of the transmission line and those of the impedance mismatch section. The remaining subsequent reflection signals are detected in a second time window having a second sampling duration corresponding to (or associated with) a length of the sensing waveguide section and a complex dielectric spectrum of the MUT.

In any embodiment of the present invention, the sensing waveguide section has a length and an open end configured to form a total reflection. An interface between the self-referencing waveguide section and the sensing waveguide section has a first effect; a length of the sensing waveguide section and a complex dielectric spectrum of the MUT have a second effect; the open end has a third effect; and the first, the second and the third effects are integrated into a characteristic boundary effect at the second interface.

Figure 6:
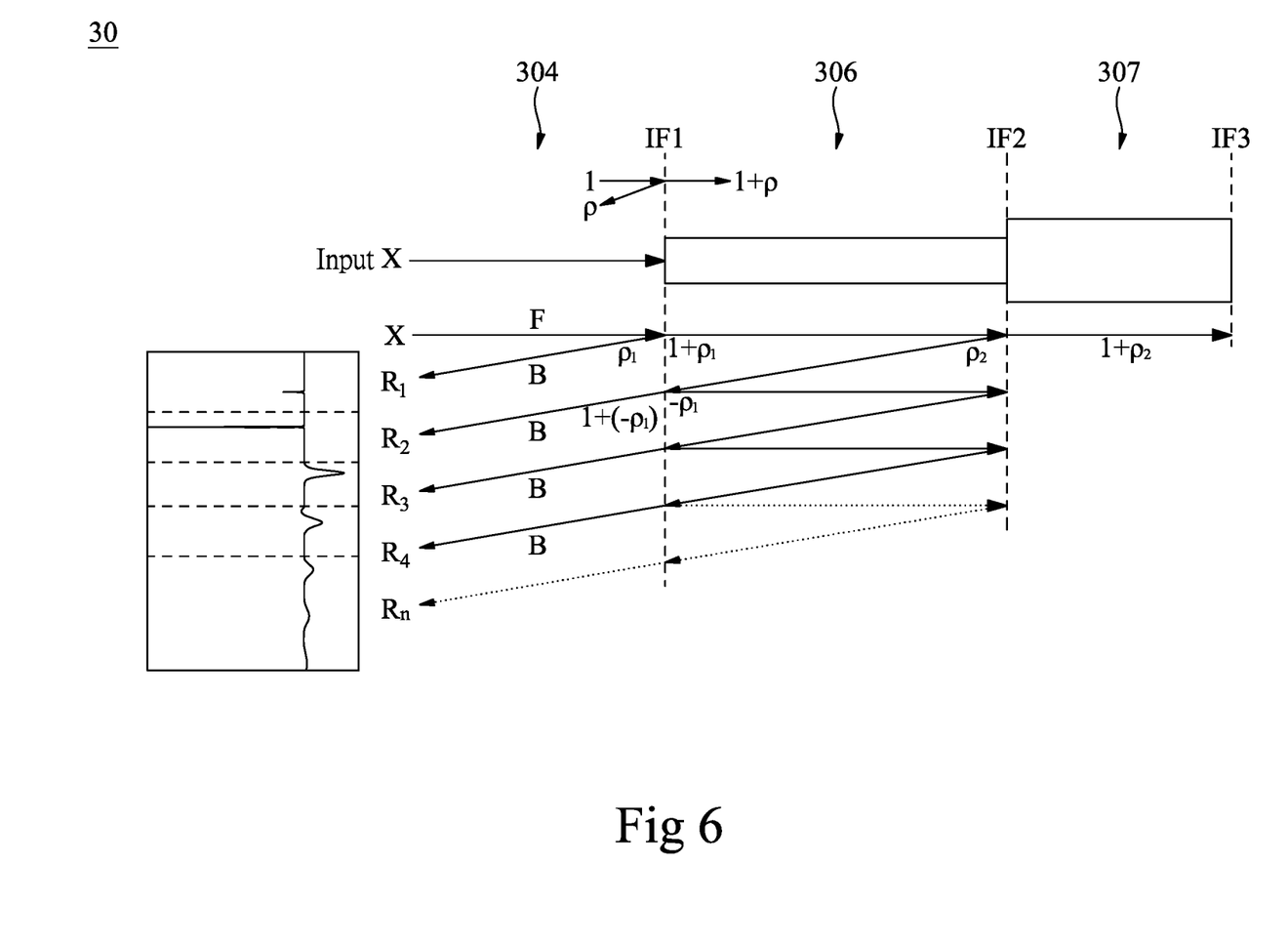
FIG. 6 is a schematic diagram showing a device for measuring the CDP of an MUT according to another preferred embodiment of the present invention.

Please refer to FIG. 6, which is a schematic diagram showing a device 30 for measuring the CDP of an MUT according to another preferred embodiment of the present invention. The device 30 includes a first medium 304, an impedance mismatch section 306, and a sensing section 307. The impedance mismatch section 306 is connected to and placed between the first medium 304 and the sensing section 307, and is characterized in that the reflection electromagnetic wave signal is transmitted to the first interface IF1 via the first medium 304 (e.g., a transmission line 4). While R1 represents the first reflected frequency component from electromagnetic wave signal X, the rest represent the remaining reflected frequency components of electromagnetic wave signal X after multiple reflection and/or transmission between the first interface IF1, the second interface IF2 and the sensing section 307, and then return to the transmission line 4, such as R2, R3, . . . , Rn, as shown in FIG. 6.

FIG. 6 also includes a schematic diagram showing the sequential time series of the received corresponding reflection electromagnetic wave signals R1-Rn. From FIG. 1 and FIGS. 2a-2b, or in FIG. 4 and FIG. 2a-2b, these figures can be integrated into a diagram as shown in FIG. 6, in order to clearly understand the time series relationship of the frequency component of electromagnetic reflection signals R1-Rn and how to decouple the frequency component of electromagnetic reflection signals R1-Rn.

As shown in FIG. 6, the effect of the electromagnetic wave signal X in the first medium 304 is represented by HLC(2LLC, ε*LC(f)), and the effect in the impedance mismatch block 306 is represented by HMS(2LMS, ε*MS(f)). The effect in the sensing block 307 is represented by HSS(2LSS, ε*SS(f)), whereas LLC, LMS and LSS represent the lengths of the first medium 304, the impedance mismatch section 6 and the sensing segment 307, respectively. ε*LC(f), ε*MS(f), and ε*SS(f) represent the complex dielectric permittivities of first medium 304, impedance mismatch section 306 and the sensing section 307 respectively. Please refer to FIG. 6 and the following equations concurrently:

$$R_1 = X \cdot F \cdot \rho_1 \cdot B$$

$$R_2 = X \cdot F \cdot B \cdot [H_{MS}(1-\rho_1^2)(\rho_2)]$$

$$R_3 = X \cdot F \cdot B \cdot [H_{MS}(1-\rho_1^2)(\rho_2)] \cdot [-\rho_1 \rho_2 H_{MS}]$$

$$R_4 = X \cdot F \cdot B \cdot [H_{MS}(1-\rho_1^2)(\rho_2)] \cdot [-\rho_1 \rho_2 H_{MS}]^2$$

$$R_k = X \cdot F \cdot B \cdot [H_{MS}(1-\rho_1^2)(\rho_2)] \cdot [-\rho_1 \rho_2 H_{MS}]^{k-2}, \text{ for } k=2, 3, \ldots, n.$$

wherein ρ2 represents the combined effect of the electromagnetic reflection signals R2~Rn within the first interface IF1, the second interface IF2 and the sensing section 307 through multiple reflections and/or transmissions.

It can be seen that $R_{remaining}$ and $R_{all}$ can be obtained through the summation of R2~Rn and R1~Rn respectively as follows.

$$R_{remaining} = X \cdot F \cdot B \cdot [H_{MS}(1-\rho_1^2)(\rho_2)] \cdot \frac{1}{1+\rho_1 \rho_2 H_{MS}}$$

$$R_{all} = X \cdot F \cdot B \cdot \left[ \rho_1 + \frac{H_{MS}(1-\rho_1^2)\rho_2}{1+\rho_1 \rho_2 H_{MS}} \right]$$

The result above is then decoupled to remove the system parameter X·F·B. For example, source function decoupling through the division method as follows: $R_{remaining}/R_1$, $R_{all}/R_{remaining}$, $R_{all}/R_1$, $R_1/R_{remaining}$, $R_{remaining}/R_{all}$, $R_{all}/R_{remaining}$. The actual operation example are as follows:

$$RDR_1 = \frac{R_{remaining}}{R_1} = \frac{\rho_2 H_{MS}(1-\rho_1^2)}{\rho_1(1+\rho_1 \rho_2 H_{MS})} \quad \text{(Equation 11)}$$

$$RDR_2 = \frac{R_{all}}{R_{remaining}} = \rho_1 \left[ \frac{1+\rho_1 \rho_s H_{MS}}{H_{MS}(1-\rho_1^2)\rho_2} \right] + 1 \quad \text{(Equation 12)}$$

where RDR stands for Reflection-Decoupled Ratio. It can be seen from Equations 11 and 12 that the system parameters X·F·B have been eliminated, leaving only the MUT-related factors and the system parameters-related factors. While the relevant factors of the system parameters are known, so the parameters related to the MUT can be measured.

In any embodiment of the present invention, the first reflection signal is used as a reference signal; the remaining subsequent reflection signals or the total reflection signals are correlated with the reference signal; and the source effect is removed or decoupled from the reflection signals by comparing the spectral ratio of two from the three reflection signals, such as the first reflection signal, the remaining subsequent reflection signals and the total reflection signal.

In any embodiment of the present invention, the measuring device is a dielectric spectrometer applied to one selected from a group consisting of: a suspended sediment concentration (SSC) measurement; an SSC measurement in high salinity environment; and fields requiring dielectric properties or dielectric spectrum characterization including material science, physical chemistry, agri-food industry, environmental engineering, geotechnical engineering, or civil engineering.

While the invention has been described in terms of what is presently considered to be the most practical and preferred embodiments, it is to be understood that the invention need not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A measuring device for multiple reflections of time-domain signals of a complex dielectric, comprising:
   an electromagnetic wave generating/receiving unit configured to generate an electromagnetic wave signal;
   a transmission line having a first characteristic impedance and connected to the electromagnetic wave generating/receiving unit;
   an impedance mismatch section having a second characteristic impedance;
   a first interface formed between the transmission line and the impedance mismatch section, wherein the electromagnetic wave signal is transmitted from the transmission line to the first interface to form a first reflection signal and a first transmitted signal; and
   a sensing section configured to measure a material under test (MUT) having a complex dielectric spectrum, wherein:
   a second interface is formed between the impedance mismatch section and the sensing section;
   the first transmitted signal is transmitted from the impedance mismatch section to the second interface, and reflected through the second interface to form remaining subsequent reflection signals; and
   the electromagnetic wave generating/receiving unit receives the first reflection signal and the remaining subsequent reflection signals to measure the complex dielectric spectrum of the MUT, wherein the measurement device is configured to use an ultrashort waveguide for highly spatial resolution point measurements.

2. The measuring device as claimed in claim 1, wherein: the remaining subsequent reflection signals are modeled by a formula as follows:

$$R_k = X \cdot F \cdot B \cdot [H_{MS}(1-\rho_1^2)(\rho_2)] \cdot [-\rho_1\rho_2 H_{MS}]^{(k-2)}$$

for k=2, 3, . . . , n, wherein X denotes the electromagnetic input signal, F denotes a first transmission effect which the electromagnetic wave signal is sent in an emission path of the transmission line, B denotes a second transmission effect which the electromagnetic wave signal is received in a receiving path of the transmission line, the relationship between the electromagnetic wave signal and the first reflection signal is denoted by a reflection coefficient ρ1, and HMS denotes a third transmission effect in the impedance mismatch section, wherein ρ2 denotes a combined transmission effect of the remaining subsequent reflection signals R2~Rn at the first interface, the second interface and the sensing section after multiple reflections and/or transmissions thereamong.

3. The measuring device as claimed in claim 1, wherein: the electromagnetic wave generating/receiving unit is configured to record a time domain signal, and includes a time domain reflectometer (TDR) or a vector network analyzer (VNA).

4. The measuring device as claimed in claim 1, wherein: the sensing section has an open end configured to form a total reflection; and
the second interface has a first effect, a length of the sensing section and the complex dielectric spectrum of the MUT have a second effect, the open end has a third effect, and the first, second and third effects are integrated into a characteristic boundary effect at the second interface.

5. The measuring device as claimed in claim 1, wherein: the first reflection signal is detected in a first time window having a first sampling duration corresponding to a length and a permittivity of the transmission line and those of the impedance mismatch section.

6. The measuring device as claimed in claim 1, wherein: the remaining subsequent reflection signals are detected in a second time window having a second sampling duration corresponding to a length of the sensing section and the complex dielectric spectrum of the MUT.

7. The measuring device as claimed in claim 1, wherein: the impedance mismatch section includes a uniform material and dielectric insulating materials or cross-section having different geometric impedances than leading section.

8. The measuring device as claimed in claim 1, wherein: the first reflection signal is used as a reference signal, the remaining subsequent reflection signals or the total reflection signals are correlated with the reference signal, and the source effect is removed or decoupled from the reflection signals by comparing the spectral ratio of two from the three reflection signals including the first reflection signal, the remaining subsequent reflection signals and the total reflection signal.

9. The measuring device as claimed in claim 1, wherein: the measuring device is a dielectric spectrometer applied to one selected from a group consisting of:
suspended sediment concentration (SSC) measurement; SSC measurement in high salinity environment; and
fields requiring dielectric properties or dielectric spectrum characterization including material science, physical chemistry, agri-food industry, environmental engineering, geotechnical engineering, or civil engineering.

10. A method for measuring multiple reflections of time-domain signals of a material under test (MUT), comprising the following steps of:
providing a self-referencing waveguide section having a front end, a back end and a sensing waveguide section connected to the back end;
generating an electromagnetic wave signal;
transmitting the electromagnetic wave signal in a first medium having a first characteristic impedance;
when the electromagnetic wave signal is transmitted from the first medium to the front end, sending a first reflection signal and a first transmitted signal from the front end, wherein the self-referencing waveguide section has a second characteristic impedance;
under a first condition that the first transmitted signal is transmitted from the front end to the sensing waveguide section, sending remaining subsequent reflection signals out through the sensing waveguide section and the back end; and
under a second condition that the first reflection signal is received in a first time window and the remaining subsequent reflection signals are received in a second time window, measuring a complex dielectric permittivity of the MUT, wherein the measurement device is configured to use an ultrashort waveguide for highly spatial resolution point measurements.

11. The method as claimed in claim 10, further including a static window selection method for analysis, wherein the static window selection method is in the first time window being independent of the MUT in the sensing waveguide section.

12. The method as claimed in claim 10, further including steps of:
performing a fast Fourier transform (FFT) on the signals measured in the first time window, the second time window and all the time windows, and respectively converting them into a first reflection wave frequency signal, remaining subsequent reflection wave frequency signals and a total reflection wave frequency signal; and
filling the sensing waveguide section with the MUT or inserting or immersing the sensing waveguide section into the MUT.

13. The method as claimed in claim 10, wherein:
the first reflection signal is detected in a first time window having a first sampling duration corresponding to a length and a permittivity of the transmission line and those of the impedance mismatch section; and
the remaining subsequent reflection signals are detected in a second time window having a second sampling duration corresponding to a length of the sensing waveguide section and a complex dielectric spectrum of the MUT.

14. The method as claimed in claim 10, wherein:
the sensing waveguide section has a length and an open end configured to form a total reflection; and
an interface between the self-referencing waveguide section and the sensing waveguide section has a first effect, a length of the sensing waveguide section and a complex dielectric spectrum of the MUT have a second effect, the open end has a third effect, and the first, second and third effects are integrated into a characteristic boundary effect at the interface.

15. A device for measuring a complex dielectric permittivity of a material under test (MUT), comprising:
an electromagnetic wave generating/receiving unit configured to generate an electromagnetic wave signal;
a transmission line having a first characteristic impedance and transmitting the electromagnetic wave signal;
a self-referencing waveguide section having a second characteristic impedance, and including a front end and a back end, wherein a first reflection signal is sent from the front end; and
a sensing waveguide section connected to the back end, and configured to cooperate with the back end to send out remaining subsequent reflection signals, wherein:
the electromagnetic wave generating/receiving unit receives the first reflection signal and the remaining subsequent reflection signals to measure the complex dielectric permittivity of the MUT, wherein the device for measuring the complex dielectric permittivity of the MUT is configured to use an ultrashort waveguide for highly spatial resolution point measurements.

16. The device as claimed in claim 15, wherein:
a first interface is placed between the transmission line and the self-referencing waveguide section, and a second interface is placed between the self-referencing waveguide section and the sensing waveguide section;
the remaining subsequent reflection signals are modeled by a formula as follows:

$$R_k = X \cdot F \cdot B \cdot [H_{MS}(1-\rho_1^2)(\rho_2)] \cdot [-\rho_1 \rho_2 H_{MS}]^{(k-2)}$$

for k=2, 3, ..., n, wherein X denotes the electromagnetic input signal, F denotes a first transmission effect which the electromagnetic wave signal is sent in an emission path of the transmission line, B denotes a second transmission effect which the electromagnetic wave signal is received in a receiving path of the transmission line, the relationship between the electromagnetic wave and the first reflection signal is denoted by a reflection coefficient $\rho_1$, and HMS denotes a third transmission effect in the impedance mismatch section, wherein $\rho_2$ denotes a combined transmission effect of the remaining subsequent reflection signals R2~Rn at the first interface, the second interface and the sensing section after multiple reflections and/or transmissions thereamong.

17. The device as claimed in claim 15, wherein:
the electromagnetic wave generating/receiving unit is configured to record a time domain signal, and includes a time domain reflectometer (TDR) or a vector network analyzer (VNA);
the sensing section has an open end or shorted end configured to form a total reflection; and
the sensing section has a second interface having a first effect, a length of the sensing section and a complex dielectric spectrum of the MUT have a second effect, the open end has a third effect, and the first, second and third effects are integrated into a characteristic boundary effect at the second interface.

18. The device as claimed in claim 15, wherein:
the measurement device is configured to use an ultrashort waveguide for highly spatial resolution point measurements;
the impedance mismatch section includes a uniform material and dielectric insulating materials or materials having different geometric impedances;
the device further comprises a dielectric spectrometer applied to one selected from a group consisting of:
suspended sediment concentration (SSC) measurement;
SSC measurement in high salinity environment; and
fields requiring dielectric properties or dielectric spectrum characterization including material science, physical chemistry, agri-food industry, environmental engineering, geotechnical engineering, or civil engineering.

19. The device as claimed in claim 15, wherein:
the first reflection signal is detected in a first time window having a first sampling duration corresponding to a length and a permittivity of the transmission line and those of the impedance mismatch section;
the remaining subsequent reflection signals are detected in a second time window having a second sampling duration corresponding to a length of the sensing section and a complex dielectric spectrum of the MUT;
the first reflection signal is configured to be used as a reference signal;
the remaining subsequent reflection signals are correlated with the reference signal; and
the source effect is removed or decoupled from the reflection signals by comparing the spectral ratio of two from the three reflection signals, such as the first reflection signal, the remaining subsequent reflection signals and the total reflection signal.

* * * * *